United States Patent
Grychtol et al.

(10) Patent No.: US 10,952,634 B2
(45) Date of Patent: Mar. 23, 2021

(54) ELECTRICAL IMPEDANCE TOMOGRAPHY SYSTEM

(71) Applicant: SWISSTOM AG, Landquart (CH)

(72) Inventors: Bartlomiej Grychtol, Mannheim (DE); Josef X. Brunner, Chur (CH); Stephan Bohm, Lauenburg/Elbe (DE)

(73) Assignee: SWISSTOM AG

( * ) Notice: Subject to any disclaimer, the term of this patent is extended or adjusted under 35 U.S.C. 154(b) by 189 days.

(21) Appl. No.: 15/027,210

(22) PCT Filed: Oct. 3, 2014

(86) PCT No.: PCT/CH2014/000143
§ 371 (c)(1),
(2) Date: Apr. 4, 2016

(87) PCT Pub. No.: WO2015/048917
PCT Pub. Date: Apr. 9, 2015

(65) Prior Publication Data
US 2016/0242673 A1 Aug. 25, 2016

(30) Foreign Application Priority Data
Oct. 4, 2013 (CH) .................................. 1710/13

(51) Int. Cl.
*A61B 5/05* (2006.01)
*A61B 5/0536* (2021.01)
(Continued)

(52) U.S. Cl.
CPC .......... *A61B 5/0536* (2013.01); *A61B 5/0809* (2013.01); *A61B 5/6831* (2013.01);
(Continued)

(58) Field of Classification Search
CPC ......... A61B 5/055; A61B 6/032; A61B 6/037; A61B 5/0073; A61B 5/742; A61B 6/5247;
(Continued)

(56) References Cited

U.S. PATENT DOCUMENTS 5,313,952 A * 5/1994 Hoch ................... A61B 5/6831
600/390
5,810,742 A * 9/1998 Pearlman ............. A61B 5/0536
600/547

(Continued)

FOREIGN PATENT DOCUMENTS

EP 1000580 A1 5/2000
GB 2400915 A 10/2004

(Continued)

OTHER PUBLICATIONS

Ferrario D et al: "Toward Morphological Thoracic EIT: Major Signal Sources Correspond to Respective Organ Locations in CT", IEEE Transactions on Biomedical Engineering, IEEE Service Center, Piscataway, NJ, USA, vol . 59, No. 11, Nov. 1, 2012 (Nov. 1, 2012), pp. 3000-3008.

(Continued)

Primary Examiner — Joseph A Stoklosa
Assistant Examiner — Brian M Antiskay
(74) Attorney, Agent, or Firm — Morriss O'Bryant Compagni Cannon, PLLC

(57) ABSTRACT

An electrical impedance tomography system for determining electric properties of an internal body part of a patient comprises an electrode array in electrical contact with the patient, a device for applying current or voltage between electrodes of the array and for measuring voltages or currents between other combinations of the array A computing unit comprises a processor and a storage unit. The storage (Continued)

unit comprises a reconstruction algorithm used by the data processor for reconstructing the measured voltages of the body part into electrical properties or changes thereof. The data processor outputs a representation of the reconstructed electrical properties and generates or processes anatomical models descriptive of the body part The data processor uses biometric data of the patient and, according to the biometric data of the patient, selects an anatomical model for reconstructing the measured electrical voltages of the body part into electrical properties or changes thereof.

27 Claims, 11 Drawing Sheets

(51) Int. Cl.
| | | |
|---|---|---|
| *G09B 23/30* | (2006.01) | |
| *A61B 5/00* | (2006.01) | |
| *A61B 5/08* | (2006.01) | |
| *A61B 5/0531* | (2021.01) | |

(52) U.S. Cl.
CPC ............ *G09B 23/30* (2013.01); *A61B 5/0035* (2013.01); *A61B 5/0531* (2013.01)

(58) Field of Classification Search
CPC ....... A61B 5/053; A61B 5/684; A61B 5/6805; A61B 5/0536
USPC ................ 600/372, 382–393, 407, 414–416, 600/425–428
See application file for complete search history.

(56) References Cited

U.S. PATENT DOCUMENTS

| | | | | |
|---|---|---|---|---|
| 8,321,007 | B2 * | 11/2012 | Teschner | A61M 16/0051 600/547 |
| 8,700,121 | B2 * | 4/2014 | Erlinger | A61B 5/04 600/391 |
| 9,060,705 | B2 * | 6/2015 | Holzhacker | A61B 5/0536 |
| 2004/0006279 | A1 | 1/2004 | Arad | |
| 2004/0077969 | A1 * | 4/2004 | Onda | A61B 5/0537 600/547 |
| 2005/0059903 | A1 * | 3/2005 | Izumi | A61B 5/0536 600/547 |
| 2006/0058600 | A1 * | 3/2006 | Eichler | A61B 5/0536 600/407 |
| 2006/0235327 | A1 * | 10/2006 | Masuo | A61B 5/0537 600/547 |
| 2010/0298687 | A1 * | 11/2010 | Yoo | A61B 5/0006 600/391 |
| 2013/0035576 | A1 * | 2/2013 | O'Grady | A61B 5/04884 600/373 |
| 2013/0096425 | A1 | 4/2013 | Uutela | |
| 2013/0102873 | A1 * | 4/2013 | Hamaguchi | A61B 5/0537 600/393 |
| 2013/0274593 | A1 * | 10/2013 | Everling | A61B 5/0536 600/421 |
| 2014/0221865 | A1 * | 8/2014 | Garber | A61B 5/0809 600/533 |

FOREIGN PATENT DOCUMENTS

| | | |
|---|---|---|
| WO | 2011021948 A1 | 2/2011 |
| WO | 2012045188 A1 | 4/2012 |
| WO | 2013110207 A1 | 8/2013 |

OTHER PUBLICATIONS

B. Brown, "Electrical Impedance Tomography (EIT)—A Review", Journal of Medical Engineering & Technology, vol. 27, No. 3, p. 97-108, 2003.

Victorino et al: "Imbalance in Regional Lung Ventilation—A Validation Study on Electrical Impedance Tomography", American Journal of Respiratory and Critical Care Medicine, vol. 169, p. 791-800, 2004.

Radke et al: "Spontaneous Breathing during General Anesthesia Prevents the Ventral Redistribution of Ventilation as detected by Electrical Impedance Tomography—A Randomized Trial", Anesthesiology 2012, 116:1227-34.

Dehghani H et al: "Incorporating a priori anatomical information into image reconstruction in electrical impedance tomography", Physiological Measurement, Institute of Physics Publishing, Bristol, GB, vol. 20, No. 1, Feb. 1, 1999 (Feb. 1, 1999), pp. 87-102.

B. Grychtol et al: "Impact of Model Shape Mismatch on Reconstruction Quality in Electrical Impedance Tomography",IEEE Transactions on Medical Imaging.,vol. 31, No. 9, Sep. 1, 2012 (Sep. 1, 2012), pp. 1754-1760.

Francois Marquis et al: "Electrical Impedance Tomography's Correlation to Lung Volume is Not Influenced by Anthropometric Parameters", Journal of Clinical Monitoring and Computing, Kluwer Academic Publishers, DO, vol. 20, No. 3, May 11, 2006 (May 11, 2006), pp. 201-207.

Dräger Beatmung Wird Sichtbar PulmoVista 500 brochure (dated 2011).

C Woitzik et al: "Ermittlung von Messdaten und Proportionen des menschlichen Thorax aus CT-Schnitten zur mathematischen Korrektur von Rohdatensatzen der Elektrischen Impedanztomografie (EIT)" Fortschr Rontgenstr Apr. 2014.

Christian Michael Woitzik, 1st ed. 2014 "Evaluierung biometrischer Patientendaten aus Thoraxcomputertomographien zur Abschatzung von mathematischen Parametern als Inputvariablen fur Rekonstruktionsalgorithmen der funktionellen elektrischen Impedanztomographie der Thoraxorgane".

Brown, B. H., Primhak, R. A., Smallwood, R. H., Milnes, P., Narracott, A. J., & Jackson, M. J. (2002). Neonatal lungs—can absolute lung resistivity be determined non-invasively? Medical & Biological Engineering & Computing 40(4), 388-394, doi:10.1007/bf02345070.

De Camargo, E. D. L. B. et al., Converting ct-scan images into resistivity measurements to form an anatomical atlas or electrical impedance tomography, 21st International Congress of Mechanical Engineering, Oct. 24-28, 2011, ABCM, Natal, RN, Brazil.

European Patent Office, Intention to Grant, European Patent Application No. 14789768.0, dated Nov. 27, 2019, pp. 1-62.

* cited by examiner

|     | 25 | 35 | 45 | 55 | 65 | 75 | 85 | 95 | 105 | 115 | 125 | 135 | 145 |
|-----|----|----|----|----|----|----|----|----|-----|-----|-----|-----|-----|
| 1.5 |    | 16 | 20 | 24 | 29 | 33 | 38 |    |     |     |     |     |     |
| 1.6 |    |    | 18 | 21 | 25 | 29 | 33 | 37 |     |     |     |     |     |
| 1.7 |    |    | 16 | 19 | 22 | 26 | 29 | 33 | 36  | 40  |     |     |     |
| 1.8 |    |    |    | 17 | 20 | 23 | 26 | 29 | 32  | 35  | 39  |     |     |
| 1.9 |    |    |    | 15 | 18 | 21 | 24 | 26 | 29  | 32  | 35  | 37  | 40  |
| 2   |    |    |    |    | 16 | 19 | 21 | 24 | 26  | 29  | 31  | 34  | 36  |
| 2.1 |    |    |    |    | 15 | 17 | 19 | 22 | 24  | 26  | 28  | 31  | 33  |

Fig. 6

|     | 25 | 35 | 45 | 55 | 65 | 75 | 85 | 95 | 105 | 115 | 125 | 135 | 145 |
|-----|----|----|----|----|----|----|----|----|-----|-----|-----|-----|-----|
| 1.5 |    |    |    |    |    |    |    |    |     |     |     |     |     |
| 1.6 |    |    | 18 | 21 | 25 | 29 | 33 | 37 |     |     |     |     |     |
| 1.7 |    |    | 16 | 19 | 22 | 26 | 29 | 33 | 36  | 40  |     |     |     |
| 1.8 |    |    |    | 17 | 20 | 23 | 26 | 29 | 32  | 35  | 39  |     |     |
| 1.9 |    |    |    | 15 | 18 | 21 | 24 | 26 | 29  | 32  | 35  | 3   |     |
| 2   |    |    |    |    | 16 | 19 | 21 | 24 | 26  | 29  | 31  | 34  | 36  |
| 2.1 |    |    |    |    |    | 17 |    | 22 |     | 26  |     | 31  |     |

Fig. 7

|     | 25 | 35 | 45 | 55 | 65 | 75 | 85 | 95 | 105 | 115 | 125 | 135 | 145 |
|-----|----|----|----|----|----|----|----|----|-----|-----|-----|-----|-----|
| 1.5 |    | C  | E  |    | G  |    | H  |    |     |     |     |     |     |
| 1.6 |    |    | 18 | 21 | 25 | 29 | 33 | 37 |     |     |     |     |     |
| 1.7 |    |    | 16 | 19 | 22 | 26 | 29 | 33 | 36  | 40  |     |     |     |
| 1.8 |    |    |    | A  | B  | C  | D  | E  | F   | G   | H   |     |     |
| 1.9 |    |    |    | 15 | 18 | 21 | 24 | 26 | 29  | 32  | 35  | 3   | H   |
| 2   |    |    |    |    | 16 | 19 | 21 | 24 | 26  | 29  | 31  | 34  | G   |
| 2.1 |    |    |    |    |    | 17 | A  | 22 | B   | 26  |     | 31  | E   |

Fig. 8

|     | 25 | 35 | 45 | 55 | 65 | 75 | 85 | 95 | 105 | 115 | 125 | 135 | 145 |
|-----|----|----|----|----|----|----|----|----|-----|-----|-----|-----|-----|
| 1.5 |    | C  | E  | F  | G  | G  | H  |    |     |     |     |     |     |
| 1.6 |    |    | C  | E  | F  | G  | G  | H  |     |     |     |     |     |
| 1.7 |    |    | A  | B  | C  | D  | E  | F  | G   | H   |     |     |     |
| 1.8 |    |    |    | A | B | C | D | E | F | G | H |     |     |
| 1.9 |    |    |    |    | A  | B  | C  | D  | E   | F   | G   | H   | H   |
| 2.0 |    |    |    |    |    | A  | A  | B  | C   | D   | E   | F   | G   |
| 2.1 |    |    |    |    |    |    | A  | B  | B   | C   | D   | D   | E   |

Fig. 8b

ELECTRICAL IMPEDANCE TOMOGRAPHY SYSTEM

CROSS-REFERENCE TO RELATED APPLICATIONS

This application is a national phase entry under 35 U.S.C. § 371 of PCT/CH2014/000143 filed on Oct. 3, 2014, which claims priority to Swiss Patent Application 1710/13 filed on Oct. 4, 2013, the entirety of each of which is incorporated by this reference.

TECHNICAL FIELD OF THE INVENTION

This invention relates to an electrical impedance tomography system according to the preamble of claim 1.

BACKGROUND OF THE INVENTION

Electrical impedance tomography (EIT) is a non-invasive imaging technique based on the injection of current and measurement of voltage through electrodes attached to the body and providing information on the internal body structures. Although this technique provides images which represent the distribution of electrical properties within the body, sometimes referred to as heat-maps, in general these images or heat maps have low spatial resolution and the correlation with the actual anatomic structure is unclear. Therefore, EIT-images are usually difficult to interpret.

Correctly speaking, Electrical Impedance Tomography (EIT) does not provide an image of impedance distribution. It provides an image of the distribution of conductivity, admitivity, impedivity, or resistivity, or changes thereof. In the following said distribution also called collectively "electrical properties". The image also called the EIT image.

Other standard imaging methods, such as CT (computer tomography) and MRI (magnetic resonance imaging)—due to the very nature and design of the devices—use their gantries as reference frame for generating their pictures. Furthermore, the patient can lie in such gantries in any position relative to such gantry with the gantry being in a constant relationship with the gravity vector. Thus, the orientation of the resulting image with regard to gravity is always the same. The actual CT or MRI image will always be shown the same way (up and down/right and left) since the gantry does not change in such orientation within the gravitational field (while the patient may take on any position). Usually the patient is in supine position.

In contrast to e.g. CT or MRI imaging, in EIT however, the electrode belt is attached to the external surface of an individual patient and—due to its fixed physical relationship with the human body—moves together with the patient.

Consequences and difficulties for diagnosis and therapy are the following:

The exact (thoracic) contour of the body part, which the belt is attached to, is unknown.

The exact circumference of the body wearing the belt is not known.

The position of the EIT electrodes on the body and thus the electrode plane relative to the gravitational vector is unknown and—as opposed to CT and MRI—mobile.

Consequently, objective and standardized EIT images are hard to come by. Pathological conditions of different patients detected by means of EIT may be hard to detect and cannot be compared readily.

In an attempt to better interpret EIT images and/or render the visual interpretation of EIT images easier, in recent studies different approaches were taken:

Moving away from a round shape typically used in back projection algorithms.

Use of generic and fixed contour in the shape of a human thorax.

Using CT, MRI or other radiographic data from an individual patient and use of these to reconstruct an individualized EIT image.

Compensation for changing patient positions relative to the gravity vector are taken into account.

In particular, publication EP 1 000 580 A1 by Ström of 2000 mentions an electrical impedance tomography system for measuring electrical impedances of an internal body section and for representing the measured data by superposing the measured impedance data onto a physical image of the same body section. By combining a conventionally obtained EIT image with a physical image, thus e.g. superposing the two, a visual correlation between the physical structure and the EIT image is perceived by the human observer. The physical image may be obtained, for example, by computer generation or by using a conventional physical imaging system, such as an x-ray system, a computer aided tomography system, a magnetic resonance imaging system, or an ultrasonic imaging system. When imaging an internal body structure whose physical properties, such as shape, size or position, may vary cyclically with time, such as will occur for instance with a heart during a cardiac cycle and lungs during a breathing cycle, it is useful to provide a number of different physical images reflecting these variations. An EIT image may then be superposed with one of the physical images selected to be closest in position in the relevant physiological cycle to the EIT image. Alternatively, the EIT image may be generated cyclically at the frequency of the relevant physiological cycle and the physical image taken at the same point in that cycle. In these ways a more accurate interpretation and correlation of a particular EIT image may be made since both the physical image and the EIT image will reflect substantially the same cyclically induced physical variations in the structure or body region of interest.

Publication EP 1 000 580 A1 discloses further that the physical images may be stored in a data store prior to the use of the EIT system and may be obtained either from the patient or from another subject, in which case the images represent generic template images of the lungs. Alternatively, a microprocessor unit could originate computer generated template images which illustrate the lungs from an algorithm which may have been constructed based on human anatomy and of the location of the belt on the patient.

However, in 2003 in order to examine the lung, it was still common to prepare a set of EIT images during a ventilation cycle and compare the multitude of EIT images at different breath cycle times with each other. This way the progressive increase or decrease in lung resistivity with ventilation can be seen. Images were presented within a circular area. A physical reference point is missing entirely, see e.g. B. Brown, "Electrical Impedance Tomography (EIT)—A Review", Journal of Medical Engineering & Technology, Vol. 27, No. 3, p. 97-108, 2003.

Victorino et al. in "Imbalance in Regional Lung Ventilation—A validation Study on Electrical Impedance Tomography", American Journal of Respiratory and Critical Care Medicine, Vol. 169, p. 791-800, 2004, compares the CT image which is accurate to body shape, and the EIT image, which is within a circular area, in juxtaposition with each other and by using a grid for sub-dividing each image into 8 schematic regions of interest. Uppermost and lowermost pixels of the contour of each of the images were taken as references, and four evenly spaced layers, each one corresponding to one fourth of the anteroposterior thoracic diameter were drawn. The mid thoracic line was determined in a similar way by division in a left and right thoracic part. Despite the grid aid, comparison of the CT and EIT images is difficult due to the differences in the shape of the seemingly corresponding regions of interest in the CT and the EIT images. Moreover, visual comparison aided by this grid reveals obvious discrepancies in the grid position between CT and EIT images. Despite the grid aid, accuracy of the contrasting juxtaposition is not satisfactory.

In 2010 the system of Dräger PulmoVista 500 uses one oval-type fixed frame (for all patients) within which the EIT image is projected for presentation of the EIT measurement data.

In 2012 a study of Radke et al., titled "Spontaneous Breathing during General Anesthesia Prevents the Ventral Redistribution of Ventilation as detected by Electrical Impedance Tomography—A Randomized Trial", in Anesthesiology 2012, 116:1227-34, the electrical impedance tomography image at expiration is subtracted from the electrical impedance tomography image at inspiration, resulting in a tidal EIT image that visualizes the two dimensional distribution of the ventilation in the thorax. Then four regions of interest are defined arbitrarily without any reference to the thoracic anatomy and the percentage of total tidal variation per region of interest is calculated.

A circular or even oval frame into which most commonly the EIT images are projected by an EIT reconstruction algorithm does not produce images which correspond accurately to the anatomy, and is therefore difficult to compare with anatomically accurate images such as from CT or MRI.

A drawback of any one of above mentioned systems and methods is the lack of a system-intrinsic positioning tool, which allows to align the EIT image with a true reference point or patient anatomy. Above mentioned image comparison is a simple display functionality based on superposition or juxtaposition of an EIT image and another physical image originating of a second but different measurement techniques. Relatively good results are achieved only when the patient is positioned accurately during the EIT measurement, i.e. in the exact same position in which the comparative measurement was taken. Moreover, as soon as a test person moves before or during the EIT measurement, the superposed or juxtaposed image will not show the correct reference in any case.

In an example EP 1 000 580 A1 shows the superposition of the individual X-ray picture of a patient with his EIT images.

Publication EP 2 624 750 discloses recording of the position of a patient with regard to the gravity vector for further consideration during analysis of the EIT data.

Furthermore, in 2012 a study of Ferrario et al., titled "Towards morphological thoracic EIT: Major signal sources correspond to respective organ locations in CT", IEEE Transactions on Biomedical Engineering, vol. 59, no. 11, 2012, compares functional EIT images with the anatomy as seen on a CT slice in the plane of the electrodes. EIT and CT measurements were taken simultaneously. A qualitative comparison was enabled by reconstructing EIT data using finite element models created by extruding in the vertical direction the outer shape of a transverse thoracic cross section (Grychtol et al., "Impact of Model Shape Mismatch on Reconstruction Quality in Electrical Impedance Tomography," *Medical Imaging, IEEE Transactions on*, vol. 31, no. 9, pp. 1754-1760, September 2012), as opposed to cylindrical ones as in the standard practice. Inner thoracic structures, such as heart and lungs, were not specifically modeled. Based on a-priori information about the exact position of the electrodes and the thoracic shape of each individual animal, electrodes were modeled at their real anatomical positions. The presented approach assured morphological correspondence between the EIT and CT images. The sources of ventilation- and cardiac-related activity in the EIT images were localized by an unsupervised method combining statistical and spectral analysis with an image processing algorithm to determine both heart and respiration rate and to define the corresponding heart and lung regions of interest (ROIs). This study shows that (a) reconstruction of EIT data on models with correct anatomic boundary shape and (b) detection of heart and lung activity using both spatial and temporal information contained within the EIT data sequence are prerequisites for correct interpretation of EIT data with regard to the functional and anatomical information contained therein.

However, in practice, the first and foremost problem of this method is that a 3D model needs to be created from a particular patient's anatomical imaging. Therefore, this is an expensive, time consuming, laborious method which may even involve specific risks such as radiation or the intrahospital transport of mechanically ventilated ICU patients.

Moreover, the models being extruded shapes are not realistic approximations to the true three-dimensional shape of the thorax.

Patent application publication US 2004/0006279 A1 discloses a method for generating impedance images of the chest, comprising: acquiring electrical data of the chest; obtaining electrocardiograph data of a patient; analysing the electrocardiograph data to obtain information about breathing parameters at the time the electrical data was acquired; and reconstructing at least one impedance image of the chest from the electrical data and the information about breathing parameters. This method is used to observe the breathing activity. The impedance images achieved with this method are similar to or even identical with those created by traditional electrical impedance images with their known limitations such as a lack of anatomical accuracy.

Patent application publication WO2011/021948 A1 discloses a gastro-electrical activity mapping system and comprising a catheter insertable through a natural orifice into the gastro-intestinal (GI) tract and comprising an array of electrodes for contacting an interior surface of a section of the GI tract to detect electrical potentials at multiple electrodes, and a signal analysis and mapping system arranged to receive and process electrical signals from multiple electrodes of the array and spatially map GI smooth muscle electrical activity as an activation time map, a velocity map, or an amplitude map, which may be in the form of contour plots and may be mapped on an anatomical computer model of at least the section of the GI tract and may be animated. The gastro-electrical activity mapping system serves to spatially map and visually display to a user GI electrical activity on an anatomical computer model of at least the section of the GI tract. This way of visualizing gastric activity does not create tomographic images as in EIT but merely projects (maps) the measured physiological signals onto their assumed anatomical structure of origin thereby providing users with visual clues intended to facilitate the interpretation of gastric activity.

ADVANTAGES OF THE INVENTION

It is an advantage of the present invention to advance EIT to a standardized and reliable diagnosis instrument, which provides reproducible, comparable and reliable results.

It is a further advantage of the present invention to provide an EIT system in which image interpretation and correlation with anatomy is improved. It is an advantage of present invention to provide an economical, time and resource saving solution.

It is an advantage of the present invention to overcome or alleviate the above-discussed drawbacks of prior art.

SUMMARY OF THE INVENTION

Said advantages are accomplished by providing an electrical impedance tomography (EIT) system for determining electric properties of an internal body section of a patient (11) comprising
- an electrode array (13) locatable in electrical contact with the body, such as an external surface, of a patient (11);
- device (15) for applying an electrical current or voltage between two or more electrodes of the electrode array (13) and for measuring generated electrical voltages and/or currents between other pair combinations of the electrode array (13);
- a computing unit comprising a data processor (19) and a storage unit (21),
- the storage unit (21) comprising at least one reconstruction algorithm for use by the data processor (19) for reconstructing the measured electrical voltages of the body section into electrical properties or changes of electrical properties,
- the data processor adapted to output a representation of the reconstructed electrical properties, and wherein
- the data processor (19) is adapted to generate and/or process a plurality of anatomical models (204) descriptive of the body part,
- the system comprises an input interface (29) for inputting biometric data (201) of the patient for use by the data processor (19),
- the data processor (19) is adapted to select one of the models from the plurality of anatomical models on account of (i.e. based on or by taking account of) the biometric data of the patient,
- the data processor (19) is adapted to use the selected model of the plurality of anatomical models for reconstructing the measured electrical voltages of the body section into electrical properties or changes of electrical properties.

Traditionally, EIT image is understood to be the representation of the (changes in) conductivity distribution in the body. However, derivative images can be created at ease by processing such EIT images to display e.g. tidal volume (as mentioned above), signal power at different frequencies or other information derived from EIT image (many examples in literature—inflection points, delay indices, etc). For the purpose of present disclosure, any such distribution may be referred to as "EIT image".

The anatomical models may be three dimensional, thus 3D anatomical models. The anatomical models, in particular the 3D anatomical models, may be based on a statistical description of the population, thus statistics based anatomical models.

In prior art, e.g. Grychtol et al (2012) and Ferrario et al (2012) mentioned above, the 3D anatomical models used for reconstructions work under the assumption that the imaged body is immutable along its vertical axis (extrusion). In contrast, herein presented models are realistic anatomical representations of the true 3D structure of the human thorax. Furthermore, the model used to reconstruct the image of an individual monitored by EIT according to present invention does not have to be this individual's truly personalized model but one that can be chosen from a pool of models using biometric data of the patient monitored by EIT.

A key feature of the system of present invention is the use of a chosen anatomical model for reconstructing an EIT image.

The anatomical model may be either 1) embedded in the reconstruction algorithm, if the algorithm has the form of a stored reconstruction matrix 2) stored and used by the reconstruction algorithm, 3) generated on the fly and used by the reconstruction algorithm. The model may be generated on account of biometric data of the specific patient and a statistical description of thorax shape in the population. Advantageously, such model can be generated for any combination of biometric data.

Biometric data (201) comprise e.g. parameters such as gender, age, race, and easy-to-obtain measurements of anatomic characteristics such as e.g. weight, height, arm span and thoracic circumference.

The biometric data (201) may comprise at least body weight and body height and optionally gender and/or age and/or thoracic circumference.

If the system is applied for children, the age plays a bigger role than in adults and hence cannot be ignored. In adults height, weight and gender seem to be needed to choose the best model. In children age becomes of particular importance.

The biometric information about the thoracic circumference (either in total or half the circumference mid spine to mid sternum multiplied by a factor of 2) obtained by a simple tailor measurement tape might further improve both: 1) the selection of the model and 2) the choice of the most appropriate size of the sensor belt for an individual patient.

Advantageously the position (203) of individual electrodes of the electrode array (13) is accounted for by the anatomical model (204), in particular in that the input interface allows input of or is adapted to read electrode array characteristics and position on an individual patient.

The anatomical model contains information about the position of the electrodes on the individual patient. Although the body (anatomy) does not change if the belt is moved, the position, size and spacing of the electrodes is critical for the success of EIT image reconstruction. The anatomical model representing the 3D structure of the thorax presented herein does account for these parameters.

Alternatively the characteristics of the belt may be predefined, without losing accuracy, if the belt is designed to have a specific and defied position with respect to the anatomy when correctly donned, in which case input or read-out of electrode array characteristics is not required.

In one embodiment the electrode array (13) is selectable from several different sizes in order to account for anatomical constitution, e.g. ranging from slim to obese.

Advantageously, the system comprises a belt carrying the electrode array (13). The electrodes of the array may be aligned in a spaced apart relationship and spread from a first belt end to a second belt end.

The system can deal with fixed distances (i.e. equidistant spacing) between electrodes as is the case in non-elastic EIT belts as well as with distances changing with breathing in elastic belts.

Placing electrodes on a belt, as opposed to free individual electrodes, fixes their relative positions. Belt types (such as e.g. disclosed in WO2013/110207) which may be used in connection with the system according to the present invention) remain in a specific and defined relationship to the anatomy. Both of these features ease the modeling task, because the electrode positions and orientations can be assumed to be known a priori. Were this not the case, laborious procedures for placing the electrodes with respect to specific anatomical landmarks would need to be in place (nearly impossible), or another system (e.g. imaging) would need to be employed to determine electrode positions.

Optionally, the belt carries an identifier, such e.g. a radio frequency identification (RFID), which is readable by the data processor. This bypasses the need for user input of belt characteristics or choice of belt size.

For example, the identifier carries information about the number of electrodes contained in the electrode array and optionally the length of the array and/or the distance between neighboring electrodes. This information may be used in generating the anatomical model, in particular the 3D anatomical model, and is relevant to processing the data originated by the electrode array, and hence EIT image reconstruction. By comparing the information contained within the identifier, such as belt length, with the user entered biometric data, such as e.g. the thoracic circumference, an estimate of the quality of the fit between the patient's body and the belt size may be estimate. For example, the belt may be detected as fitting perfectly, or being too long, or too short, for a given patient. This information can then be used in generating the anatomical model to improve the correspondence between electrode placement on the patient and the model.

Advantageously, the distances between neighboring electrodes of the electrode array (13) are predetermined. The distances between the electrodes of the electrode array (13) may be the same or the higher distance values are a multiple of the lower distance values.

The reconstruction algorithm may be adapted to take account of the number and position of electrodes comprised in the electrode array. Moreover, the reconstruction algorithm is adapted to take account of the number of electrodes actually in contact with the subject's body.

Normally, the positions of the electrodes as far as the algorithm is concerned are fixed by the anatomical model, in particular the 3D anatomical model (unless the algorithm modifies the anatomical model, in particular the 3D anatomical model).

For example, the reconstruction algorithm is adapted to take account of the number of electrodes comprised on the electrode array, in that, when the belt is mounted on a patient, in a situation where two electrodes of each end of the belt overlap each other, for the purpose of the reconstructions at least one of the two overlapping electrodes is considered to be mute, i.e. electrically disconnected.

The system according to present invention further can comprise a sensor for determining the orientation of the EIT measurement plane with respect to the gravity vector, in particular for determining the spatial orientation of the body section of the patient. For example, for this purpose a sensor device like the one disclosed in publication EP 2 624 750 (the disclosure of which is incorporated by reference herein in its' entirety) may be used.

In contrast to conventional CT and MRI imaging, in EIT, the orientation will change with any change of the patient's body position as the electrodes are attached to the patient's body. The herein presented new system allows for presentation of the EIT data with regard to the gravity vector.

Since gravity is one of the key factors affecting the state of expansion of the lung tissue with increasing collapse along the gravitational vector, the gravity-dependent display of EIT images is of the essence for their correct interpretation, which could trigger gravity-modulating therapies such as patient positioning or modification of airway pressures such as PEEP.

Advantageously, the electrode array (13), such as the belt, carries the sensor for determining the orientation.

The data processor (19) may be adapted to use position data as input for a display algorithm in order to display patient position.

The processor may be adapted to display the representation in alignment with the gravity vector and/or in respect to an indicator of the gravity vector, so that the position of patient at the time of measurement is apparent from the display.

Advantageously, the data processor (19) is adapted to output a cross-section image (107) of the anatomical model in the plane of EIT measurement.

The cross-section image comprises contours of the external body and internal organs. The contours delineating organs advantageously are overlayed on (i.e. overlay) the EIT image. The cross-section image or rather these contours are derived from the anatomical model (i.e. representing the outer boundaries of the modeled organs within the electrode plane), and hence from a mathematical description in terms of biometrics, rather than a segmentation of the specific patient's anatomical imaging, such as CT- or MRI-slices or scans. The cross-section image (207) shows expected thorax and organ contours in the measurement plane.

The anatomical matching of the model and the displayed contours derived from it bear the great advantage that the functional information obtained by EIT can now be projected into the anatomical context. This does not only facilitate their visual interpretation but can also be used to automatically interpret the EIT signals obtained since the contours of functional structures can be used to (automatically) cluster the pixels within such structures to form Regions Of Interest (ROI) that match functionally meaningful anatomical structures such as heart, lungs and aorta. Signals of pixels falling within such ROIs can be easily identified and analyzed separately for each one of the ROIs by automatic signal processing means and algorithms. The result of such ROI-based analysis can either be shown for each pixel within such ROI separately or as one global number (or in a case of a series of EIT images as a time course) representing the entire ROI.

Advantageously, the processor (19) is adapted to generate for display a superposed combination of the representation (208) and the cross-section image (207) of the anatomical model.

The advantages of overlaying the contours are:

Showing to the user what the expected extent of each organ is, which aids interpretation.

Areas within i.e. the lung contours that do not show ventilation activity in the EIT image may be indicative of lung collapse or of lung overdistension. Such mismatch between the EIT image and the respective lung contour (under normal circumstances both, EIT image and contours should match more or less perfectly) acts as a visual trigger for the caregiver to search for the underlying cause of such discrepancy and to initialize appropriate treatments.

Allowing the user to detect a situation where the image is unrealistic (usually resulting from imperfect electrode contact or external disturbance to the system).

Allows organ-specific analysis of the EIT image by grouping its pixels based on the contours they fall into.

Additionally the electrode positions can be superposed onto the representation, i.e. on the EIT image.

In prior art document EP 1 000580 A1, a "physical image" (CT, MRI, or computer generated look-alike) is used to create a "superposed combination" showing "visual correlation" on a raster image basis (i.e. pixel-based). In contrast, present inventive system does not use an image, but rather a contour of body and organs, whose shape is adapted to the individual patient.

The contours can be used to group pixels of the representation (i.e. EIT image) based on which contour they fall in and optionally the various metrics (such as e.g. amplitude of change or time course display) are calculated for each group of pixels. Typically the areas within the contours are called "Regions Of Interest". Thus, pixels falling within a respective contour comprise or define (anatomically-related) ROIs.

Generally, on an EIT image, one does not know the extent of each organ, and thus for any given pixel, one does not generally know what physiological process or organ influences its value. In the system of present invention, it is known which pixels of the image represent which organ (thanks to the contours) and, therefore, these regions of the image (groups of pixels) can be analyzed (e.g. by calculating average/minimum/maximum value, histograms, change over time) separately. For instance, according to present invention it is now possible to provide a tidal volume for the right and left lung separately, or display the change with time of the heart pixels only.

Normally, the representation (208) is an image or matrix of the distribution of the electrical properties, that may be adapted for display in form of a heat map, whereby the values of the matrix are turned into a heat map. Heat-maps are derived by processing series of one or more EIT images of the same patient.

A heat-map does not represent a physical object but rather "states" of a physical object, here e.g. the functional state of the breathing lungs. Function or action is not anatomy (or morphology). A heat map only makes sense, if the underlying structure, i.e. in particular the anatomical structure, is known. While conventional EIT monitors lung action or function, it remains uncertain where in the thorax exactly the action happens. The new system according to present invention provides an anatomical reference for the measured EIT data, so that action (or function) and anatomy can be linked. Thus, the new system according to present invention links EIT data pixels to a mathematical mesh point of the anatomical model. In summary it can be said that the system of present invention brings changes of electric property (as a reflection of organ function) and anatomy of said organ together. For this reason the system according to present invention allows to display lung function in a lung model at accurate location; such display may be called heat-map.

The storage unit (21) may comprise information for providing the plurality of anatomical models for use by the data processor (19) for reconstruction, wherein the information is provided e.g. in a library (25) or within an algorithm such as e.g. the reconstruction algorithm (23).

Advantageously, the processor is adapted to generate or recall from storage the plurality of anatomical models (204) on account of biometric data of an individual patient (201) and of biometric data of a population (102).

The key link here is that the biometric data of the individual patient are used to select from a representative cohort of patients (to which this patient should belong) the model matching best. Therefore, the choice of the population is essential and precludes use of the inventive methods in cases in which the patient does not belong to such population (i.e. for children another set of models must be used which is generated i.e. for each age group and gender separately). For example in a tested population of adult Caucasians (adults from central Europe), age did not seem to be a key factor influencing the modeling. Therefore it was possible to simplify the system, by removing the parameter age from the set of biometric data needed for the selection process. This is advantageous since it eliminates the need for additional sets of age-specific anatomical models. In the tested adult population "one age fits all". However this finding is not necessarily true in children or other populations or races such as Asians, Africans etc.

The processor may be adapted to generate the plurality of anatomical models (204) on account of a statistical description of the population and information on the individual patient and information on the electrodes. Hereby the statistical description of the population comes from CT, MRI or equivalent data and biometric data.

The processor may be adapted to generate the plurality of anatomical models (204) on account of
shapes of organs of a standardized ribcage (108), and
mathematical relationships (111) describing statistical relations between biometric data (102) and shapes of body and organ of a population. There is a plurality of shapes, in that there is one average shape for each (relevant) vertebra in the spine. Thus, the shape of the organs within the anatomical model is variable along the patient's vertical axis, as is its outer surface, and thus more representative of the true thorax shape.

As mentioned above the idea is to cover the widest possible range of patients with one set of anatomical models, in particular 3D anatomical models, and only adapt this set of models if it no longer becomes representative of the individuals of the underlying population from which it was generated. However, it can be advantageous to limit the population to a specific age group of children and/or a specific race or other criteria, in order to customize the anatomical model and therewith the system of present invention for a specific user group (i.e. patient group).

The "standardized ribcage" is meant to represent a rectangle of defined proportions, the specific proportions being irrelevant, into which organ contours segmented from transverse images from an anatomically accurate medical imaging modality are fitted prior to calculating their average by independently scaling their width and height such that they equal those of the rectangle. This is further described in the paragraph "Data processing" and the associate FIG. 2 below.

In a one embodiment the mathematical relationships (111) account for biometric data (102) of a population and anatomical data (101), e.g. CT-scan data, of a population, in particular the same population. For every patient in the dataset of the scan that form a sample of the population, both biometric data and CT data are required.

Advantageously, the organ shapes of a standardized ribcages (108), originate from anatomical data (101), e.g. CT-scan data.

Optionally, the processor (19) is adapted to use a lookup table (202) to select an anatomical model, the lookup table (202) comprising
exemplary cross-section contour models for some combinations of body height and body weight, such as for a constant body height,
a rule for indication of tracks (dotted lines in FIG. 8) between various coordinates of body height and body weight connecting those coordinates relating to cross sectional contours of empirically assumed constant dimensional proportions.

The lookup table is one way in which a particular anatomical model may be chosen for a particular patient.

Separate exemplary cross-section contour models may be used for different gender and/or different age groups.

Advantageously, the processor (19) selects a model on account of the biometric data (201) of an individual patient.

Optionally, the processor (19) is adapted to select from at least two gender specific lookup tables (202). Alternatively, the lookup tables may be age-specific and/or race-specific and/or specific with respect to other features, such as in combination with the mentioned gender specificity.

The exemplary cross-section contour models can range from a slim type to an obese type, such as at least for a constant body height.

The key point is that such models now take into account the relative position of each one of the electrodes with respect to the internal structures/organs. For adults, the size of such internal structures correlates with body height but not with body weight since organs do not grow as patients gain weight. The results of knowing the position of the electrodes with respect to the organs they monitor will be better EIT mages which are more reliable, more representative and more robust.

A means for providing anatomical data can comprises any one of x-ray computed tomography systems, magnetic resonance imaging systems, or any other imaging modality capable of providing anatomically accurate cross-sections of the human body.

In a way present inventive system allows to monitor and map the functional status of a breathing lung. State of the art EIT imaging reveals changes in the lung of a breathing patient, however a correct link to the morphological location of action is not possible. In contrast thereto, present invention provides a link between the morphology and the activity of an organ such as e.g. the lung or heart. In particular, present invention provides the reference from an anatomical model (in particular a 3D anatomical model), i.e. a mathematical mesh, as well as from a display point of view. Meaning that, firstly, the EIT image has the shape of the thorax and, secondly, the organ contours are overlain onto the image to aid interpretation.

Present invention uses data from another imaging technique than EIT, here in particular CT (computer tomography), in order to establish a means of generating models representing the inner conductivity of a body section in 3D for individual patients. These models are used to calculate the EIT images. In order to aid interpretation, for display, the organ contours (which are separately derived from the same 3D models) are overlaid onto said EIT image. This way effectively, rather than showing (a combination of) two images, present inventive system allows for annotation of the EIT image in order to indicate to a user what is (supposed to be) where. This method is fundamentally different from the conventional way of visually comparing an EIT image with a reference image, irrespective of whether the reference image is a picture of the relevant patient or a standardized template.

The EIT system according to present invention opens up new fields of application for the EIT technology. Situations in which gravity is a relevant factor, for diagnosis and eventually also for therapy the effects of gravitation must be taken into account. With present new EIT system this becomes possible because now it is possible to represent EIT results with respect to true body orientation and position.

BRIEF DESCRIPTION OF THE DRAWINGS

An embodiment of the present invention will now be described by way of example only with reference to the figures, in which, schematically

FIG. 6 shows a body mass index (BMI) table.

FIG. 7 shows a body mass index (BMI) table plus selection of best-fit tomograms for males.

FIG. 8 shows a body mass index (BMI) table plus selection of best-fit tomograms for males. Letters A to H indicate base thoracic cross-sections.

FIG. 8*b* shows a similar table as in FIG. 8, with the body height at the ordinate and respective body weight at the abscissa.

DETAILED DESCRIPTION OF THE INVENTION

Figure 1:
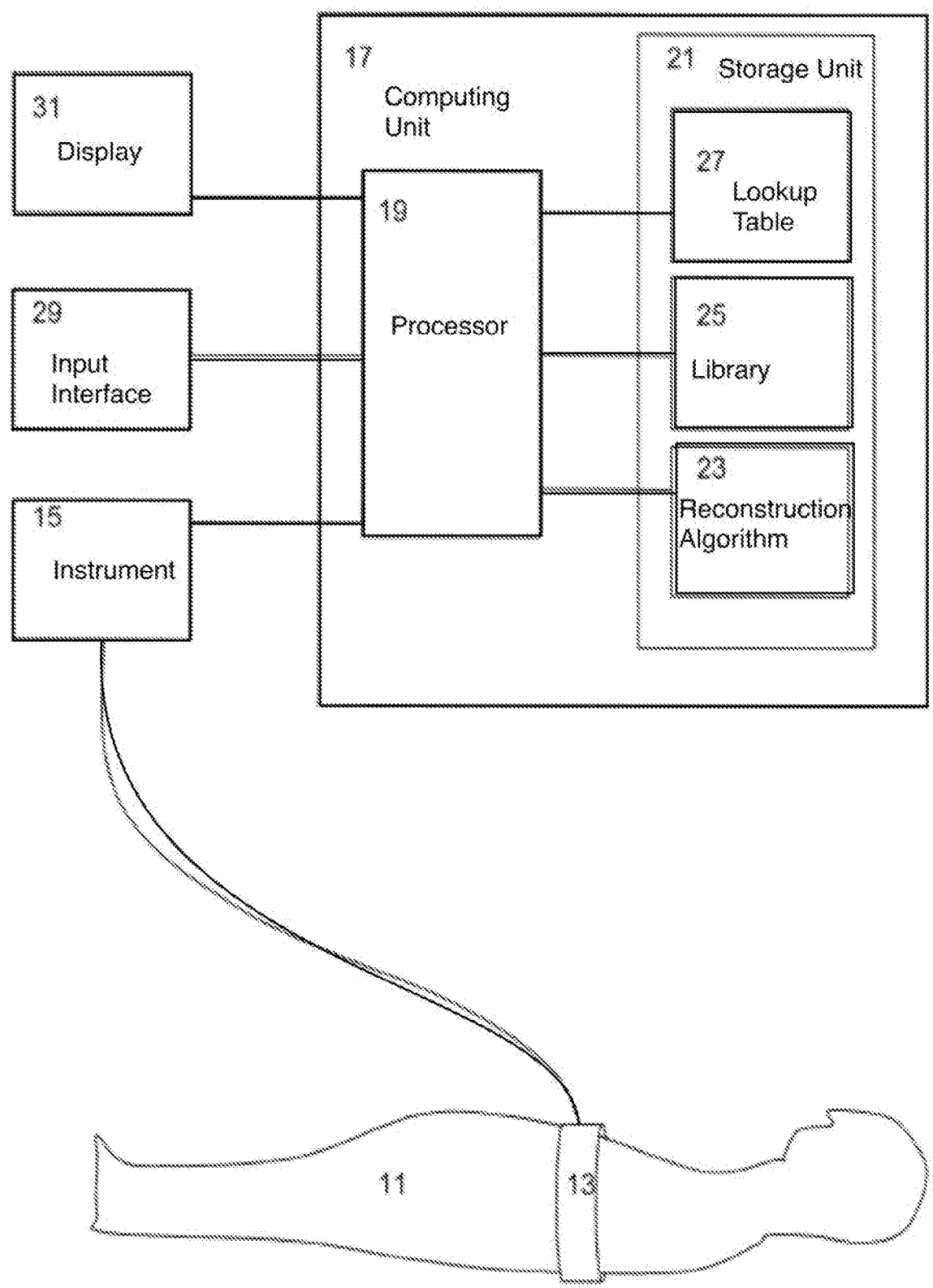
FIG. 1 shows an EIT system according to present invention.

In FIG. 1 an electrical impedance tomography (EIT) system according to present invention is presented. The system comprises an electrode array, which is locatable in electrical contact with the skin surface of a patient 11. The electrode array is attached to a belt 13, which is positioned around the patient's thorax. The system further comprises an instrument 15 for applying voltage or current to two or more of the electrodes of the electrode array and for measuring voltage or current between pairs of electrodes of the electrode array. For example, instrument 15 stimulates the patient's body with current (or, equivalently, with voltage), and measures voltage (e.g. potential differences between pairs of electrodes or between individual electrodes and the ground). The measured signals are transmitted to the computing unit 17, which comprises a processor 19 and a storage unit 21. The processor 19 uses the measured voltages, an anatomical model (i.e. a model of the body), and a model of the physics to reconstruct an image of the conductivity (or admitivity) distribution within the patient's body section circumvented by the belt 13. Although that image is most often presented as 2D raster (pixel-based) image, it could in principle be three-dimensional.

In the context of EIT, image reconstruction is understood as a method to calculate (recover, i.e. reconstruct) electrical properties (or changes thereof) inside a volume from (electrical) data acquired at its surface.

The storage unit 21 comprises at least one reconstruction algorithm 23. The reconstruction algorithm 23 is used by the data processor 19 for processing the measured electrical voltages of the examined body section into electrical conductivities by reconstructing the measured electrical voltages onto a section of the anatomical model. One or several anatomical models may be part of the algorithm (i.e. embedded in the algorithm) or stored in the storage unit 21, e.g. as a library 25 of a set of anatomical models. The anatomical models are descriptive of the three dimensional body section as well as electrode placement on it. In particular, described are external body shape, e.g. thorax, and organ shapes, e.g. lungs and heart, as well as the mutual arrangement of these shapes. The plurality of anatomical models comprises a set of standardized anatomical body section models of the thorax. The different models of the plurality of anatomical models are distinguished from each other by their anatomical composition and shapes and/or the electrode characteristics (spacing, size, number, position, orientation, etc.). The anatomical model is e.g. a model of a thorax. For reconstruction a 3D model in the form of a tetrahedral mesh is used. For reconstruction the anatomical model is enhanced by linking mesh element to physical properties, such that each mesh element is linked to a conductivity value. Furthermore, there might be foreseen several libraries (25) which are limited to a combination of gender, age, race and/or other relevant biometric parameter.

Optionally, the storage unit 21 comprises a lookup table 27. Such lookup table may comprise a pool of preset biometric data to choose from, corresponding to the anatomical models stored on the device. "Anatomical composition" means the mutual position of organ contours and external body contour. For example in the body section of the thorax the anatomical composition comprises the mutual position of lung, heart and thoracic contours. "Anatomical shapes" means the shapes of organ contours and the shape of the external body contour. For example in the body section of the thorax the anatomical shapes comprise the shape of the lung contour, the shape of the heart contour and the shape of the thorax contour. Besides the mentioned organs, further organs may be taken into account, such as e.g. ribs or aorta.

The anatomical model of the body is a discretization of the imaged volume of the body into finite elements (here: tetrahedral), each associated with a function (here: constant) describing the distribution of conductivity within that element. Internal boundaries within the volume (such as between organs) are mirrored in the model in that no finite element crosses an internal boundary.

The system comprises an input interface 29 for inputting biometric data of the patient. The biometric data of the patient are used by the data processor 19 to select the anatomical model from the plurality of anatomical models stored in the data base 25, which describes the thorax of the patient best.

A thoracic cross-section which corresponds to the body plane circumvented by the electrode array belt is displayed on a displaying means 31, e.g. on a monitor. This thoracic cross-section is computed on account of the anatomic model. At the same time a representation of the reconstructed (changes in) electrical conductivities (or another electrical property, such as e.g. admitivity, impedivity, or resistivity) is displayed on the displaying means 31. The cross-section and the representation may be combined into a superposition.

The system according to present invention serves to determine and present electrical property distribution, or change thereof, of an internal body section of a patient 1. Image reconstruction technique is applied in order to compute the distribution.

Image reconstruction in electrical impedance tomography (EIT) is a severely ill-posed inverse problem. In medical applications, because of uncertainties about the exact positioning of electrodes as well as the shape of the patient's body, EIT images are characterized by low spatial resolution and uncertainty regarding signal source locations. However, recent research (Grychtol et al. 2012 mentioned above, Ferrario et al. 2013 mentioned above) demonstrated that the quality of EIT images can be improved by incorporating in the reconstruction algorithm a model of the patient's own body surface, together with electrodes. Such a model could be derived from prior imaging of the patient with anatomically-accurate modalities such as X-ray computed tomography (CT) or magnetic resonance imaging (MRI). This is obviously impractical as not all potential EIT patients undergo such diagnostic imaging and requiring it for EIT is not an option due to prohibitive costs, time constraints and radiation exposure. Fortunately, it has been shown that the geometry incorporated in the reconstruction algorithm need not be matched exactly; small inaccuracies are well tolerated and do not have a detrimental effect on functional lung EIT images (Grychtol et al. 2012 mentioned above). For the purpose of the practical application of EIT, it was found that an appropriate model for a given patient can be chosen from a library based on the patient's biometric data.

In the following are described the creation of such a library. First, measurements are extracted from segmented transverse and sagittal anatomical images (MRI or CT) for a group of patients (Paragraph "Data processing"). Second, statistical predictive models for those measurements are constructed using the patients' biometric data as independent variables (Paragraph: "Statistical analysis"). Third, a method is devised to programmatically generate approximate segmentations of transversal slices of the human thorax given a person's biometric data and the slice position relative to the spine (vertebra number) (Paragraph: "Building an approximate slice"). Fourth, based on so obtained slices, a number of 3D geometric models of the human thorax are generated (the shape library) (Paragraph: "3D models"). Last, a scheme is described to choose an appropriate model for individual patients (Paragraph: "Creation of a lookup table").

Data

Data consists of a) transversal tomographic slices of a sample of patients (i.e. CT, MRI or EBCT or any future modality that can do so), spanning a wide range of ages, bodily structures and body mass index (BMI) values, where a small number of slices crossing different vertebrae for each patient are segmented; and b) longitudinal slices showing the spine of a possibly different population of patients. On each transverse slice the following structures are segmented (outlined), if visible: body outline, left lung, right lung, heart, sternum, and vertebra. On sagittal slices the center of each intervertebral disk is marked.

Data Processing

Figure 2:
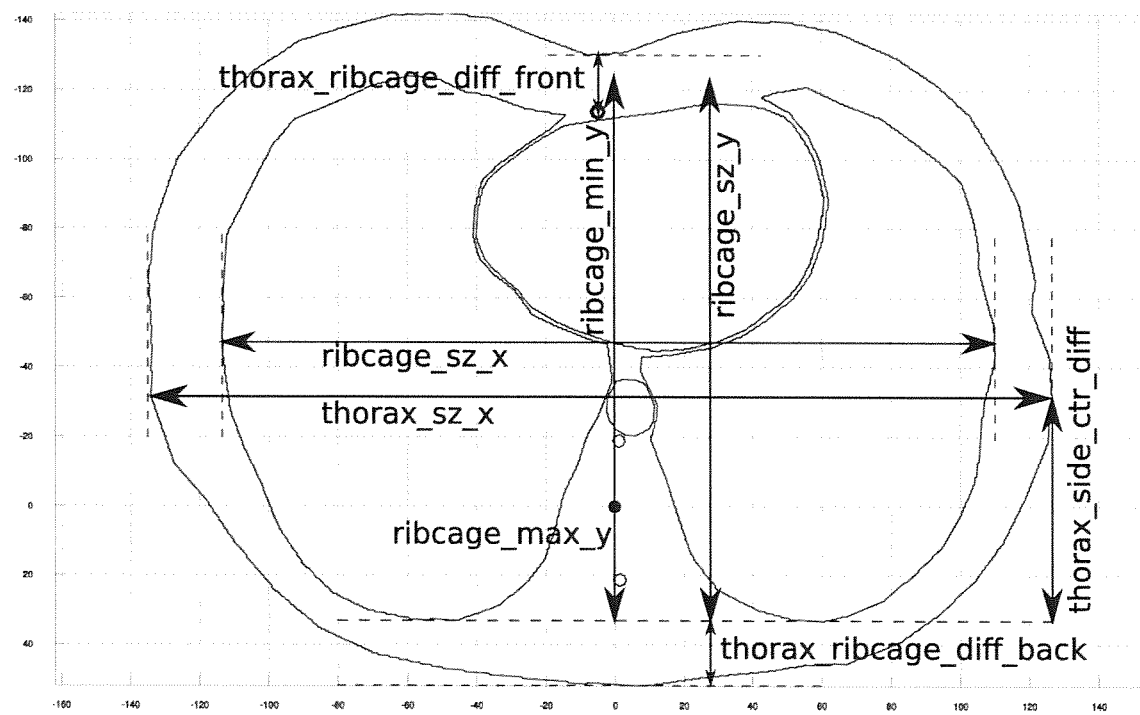
FIG. 2 shows sample contours from a single CT slice. The measurements used for analysis are indicated with arrows.
Figure 3:
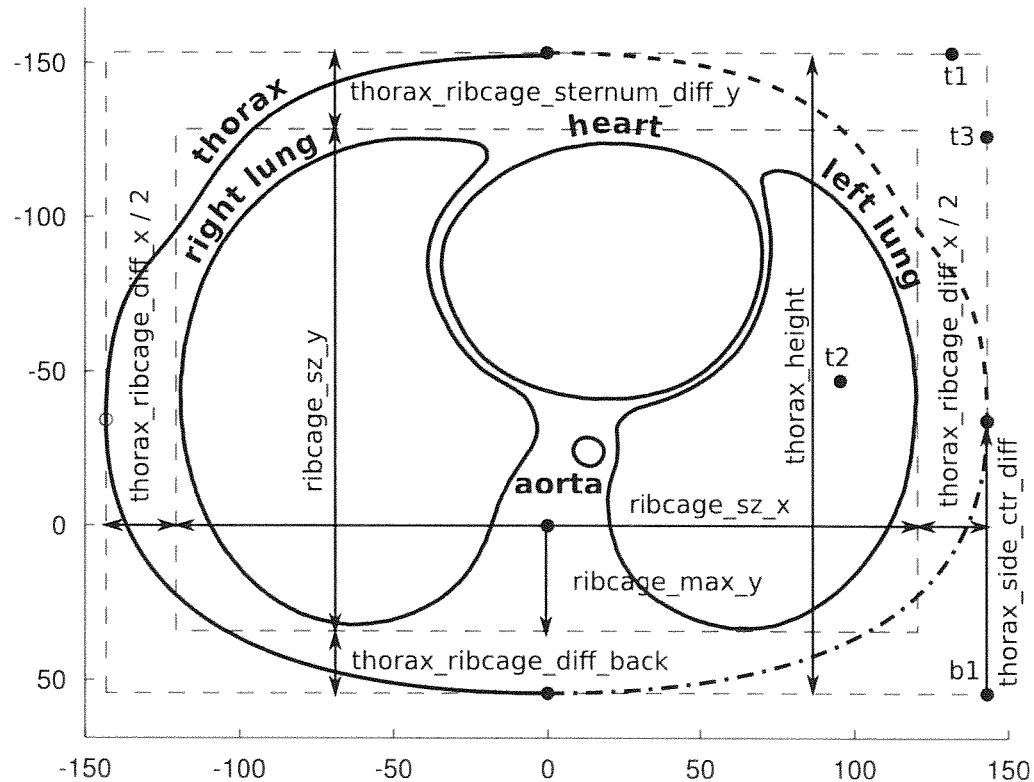
FIG. 3 shows a contour reconstruction. The measurements predicted by regression models are indicated with arrows. The top right spline segment is shown with a dashed line and its three control points are marked t1-t3. The bottom right spline is shown in dash-dot line, and the single control point is marked b1.

Before measurements of Distances and control point weights as per FIG. 2 and FIG. 3 for statistical analysis are extracted from the segmentations ("contours"), they are pre-processed such that the average vertebra on all slices of the same patient is vertical, and its center coincides with the origin of the coordinate system.

Furthermore, after alignment and extraction of measurements for statistical analysis, the contours of the organs (lungs and heart) are scaled such as to fit in a common bounding box (dashed inner rectangle circumscribing the lungs and heart in FIG. 3) and grouped according to the vertebra intersected by the originating slice. Sets of average organ contours, one per vertebra, are calculated.

Parametric Description of the Thorax Contour

Because the outer thorax shape varies widely in humans, and because this shape has a very strong influence on the quality of EIT images, it does not make sense to describe the thorax as an average shape in the same way as the inner organs. Instead, a more flexible parametric description is required. The challenge is, however, to develop a description with few parameters that can be estimated from the available data, while striking a balance between goodness of fit and generalizability.

The thorax contour is described as a closed rational Bézier spline, that is a series of curved segments described by two end-points and one or more control points, not generally lying on the segment, which control its curvature. A Bézier spline of degree n is a function $B(t) \in \mathbb{R}^2$, where t is the normalized spline segment length $0 \leq t \leq 1$, given by the equation $$B(t) = \frac{\sum_{i=0}^{n} b_{i,n}(t) w_i P_i}{\sum_{i=0}^{n} b_{i,n}(t) w_i}. \tag{1}$$

where $b_{i,n}(t)$ are the Bernstein basis polynomials $$b_{i,n}(t) = \binom{n}{i}(1-t)^{n-i}t^i \tag{2}$$

and $P_0 \ldots P_n$ are the successive points defining the segment, $P_0$ and $P_n$ being the endpoints, each with an associated weight $w_i$.

The thorax contour is defined as four spline segments (FIG. 3). The segments' endpoints are divided by the dorso-ventral axis passing through the vertebra center and a perpendicular horizontal (left-right) axis at the level where the thorax is the widest. Thus, each segment describes one thorax "quadrant". As the thorax is assumed to be left-right symmetric, only two quadrants need to be defined (e.g. top-right and bottom-right).

The bottom quadrants are defined by a quadratic spline with one control point b1, located at the corner of the thorax bounding box. The endpoints have a fixed weight of 1, whereas the weight of the control point is variable.

The top quadrants are defined by three control points ($4^{th}$ degree spline). The first control point t1 is located on the ventral side of the thorax bounding box at a distance away from the sternum equal to half the average width of the ribcage and thorax bounding boxes. The second control point t2 is inside the ribcage bounding box. Vertically, it is located at the midline of the ribcage bounding box; horizontally, it is removed from the side of the bounding box by the distance between the sternum and the ventral side of the thorax bounding box. The third control point t3 is located on the right (left) side of the thorax bounding box; it is removed from the endpoint defined by the widest point of the thorax by distance d given by the formula:

$$d = \frac{2}{3}\left(\text{ribcage\_max\_y} - \text{thorax\_side\_ctr\_diff} - \frac{1}{2}\text{thorax\_height}\right) \tag{3}$$

where thorax_height is the height of the thorax bounding box (dashed outer rectangle in FIG. 2). This formula is designed to place the control point below the line defined by the ventral side of the ribcage bounding box. The weights for both endpoints and the last control point are 1; the weight of the first control point is 1.5, while the weight of the middle control point t2 is variable.

The parametric contour descriptions are fitted to the segmented thorax contours by setting the point locations according to their definitions and adjusting the variable weights of control points b1 and t2 such as to achieve the best possible fit, i.e. minimize the non-overlap area. Thus obtained weights are added to the data set for statistical analysis.

Statistical Analysis

From each segmented slice ("contours"), a set of measurements is extracted, described in the next section. These are used as dependent variables in a series of ordinary linear regression models. In each model, predicting one measurement, the independent variables are selected from: other extracted measurements, vertebra level of the slice, and the patient's biometric data: age, gender, height, weight and BMI. Additional independent variables are created by linear combinations and squares of those listed.

Machine learning methods other than ordinary least squares regression could be used just as well. The type of model used has no bearing on the process.

Building an Approximate Slice

The generation of approximate transversal slice of the human thorax crossing a given vertebra proceeds in the following steps:

Prediction of the width and height of the bounding box of the ribcage (ribcage_sz_x and ribcage_sz_y).

Prediction of the distance between the dorsal side of the bounding box and the vertebra center (ribcage_max_y).

Scaling of the average organ contours to fit the ribcage bounding box. At this stage the ribcage is complete and positioned in the coordinate system centered on the vertebra center. In FIG. 2 and FIG. 3 the point (0,0) represents the vertebra center; the vertebra itself is not drawn since it is not part of the model.

Prediction of the difference in width between the thorax bounding box and the ribcage bounding box (thorax_ribcage_diff_x (which is the sum of thorax_ribcage_diff x/2 and thorax_ribcage_diff x/2, see FIG. 3)).

Prediction of the distance between the ventral side of the thorax bounding box and the sternum (assumed to be on the ventral side of the ribcage bounding box) (thorax_ribcage_sternum_diff_y).

Prediction of the distance between the dorsal side of the thorax bounding box and the dorsal side of the ribcage bounding box (thorax_ribcage_diff_back).

At this stage the bounding box of the thorax contour is defined and positioned.

Prediction of the distance along the ventro-dorsal axis between the dorsal side of the ribcage bounding box and the widest point of the thorax (thorax_side_ctr_diff).

Prediction of the control point weights (thorax_cp_w_top and thorax_cp_w_bot).

Plot of the thorax contour within the bounding box using the spline definition described above (FIG. 3).

An example approximate transverse thoracic slice generated as described is presented in FIG. 3

3D Models

Figure 4:
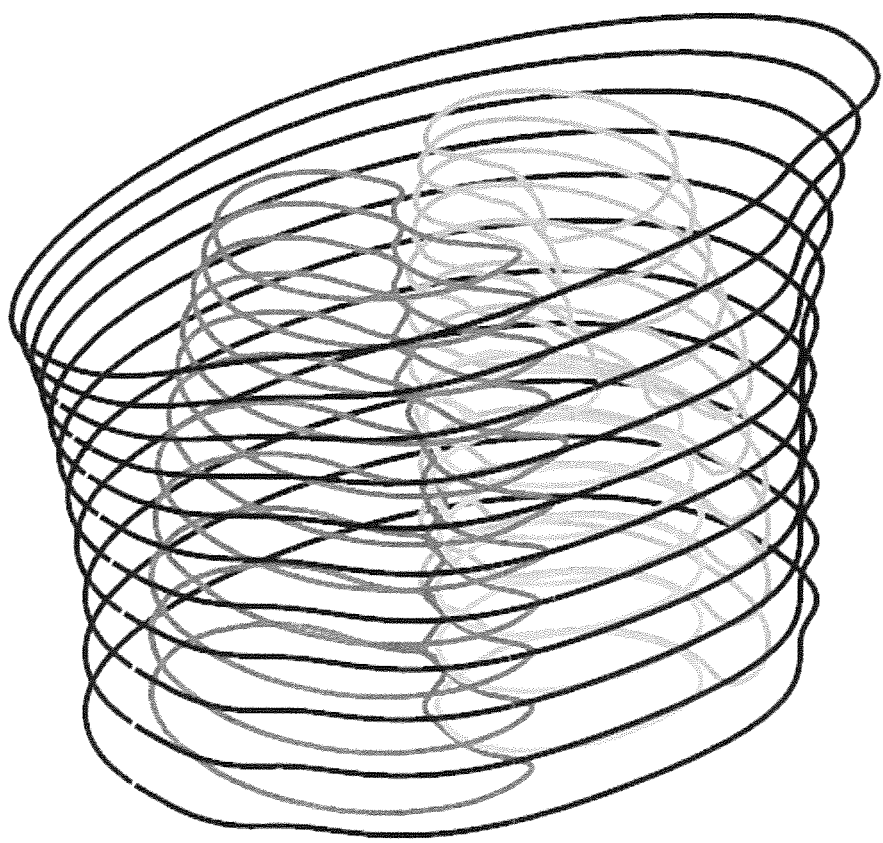
FIG. 4 shows a cross-sections of the 3D model based on the predicted contours and vertebrae heights.

The 3D anatomical models are tetrahedral finite element models (FEMs) of the thorax between vertebrae T3 ($3^{rd}$ thoracic vertebra) and L1 ($1^{st}$ lumbar vertebra), including internal organs. The height of the model in caudal-cranial extension is calculated by summing the predicted heights of the vertebrae. Horizontal cross-sections of the model at the heights of vertebra centers correspond to the respective approximate slices created using the above procedure, as in FIG. 4.

Figure 5:
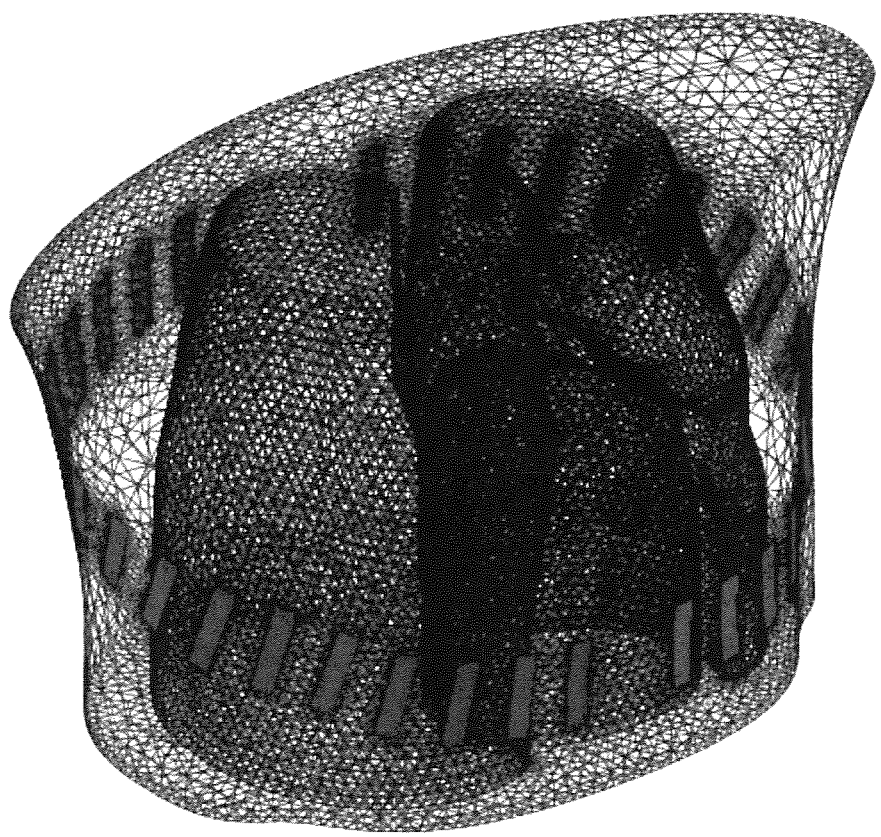
FIG. 5 shows a complete 3D anatomical finite element model.

Based on the expected positioning of an electrode belt and its geometry, electrodes are included at the surface of the model with local FEM refinement for better simulation accuracy when used as the forward model in an EIT reconstruction algorithm, see FIG. 5.

Creation of a Lookup Table

Above described models could, in principle, be generated for any combination of a set of biometric data describing a patient. While this is significantly faster and easier then generating the required 3D models from anatomical imaging of a given patient as in prior art, further optimization is possible, since some variations in biometric data have little influence on the resulting model, and required, since the models still have a generation time of several minutes and require considerable computational power to generate.

According to present invention, a number of 3D models for a plurality of pre-set combinations of biometric data are stored on the device. An appropriate model for a given patient is then chosen from a lookup table 202 (FIG. 11) based on the given patient's biometric data and the available models. The following describes the creation of such a lookup table.

An empirical quantization of body height and body weight in steps of 10 cm and 10 kg from 150 cm to 210 cm and 35 kg to 145 kg for men yielded the BMI table of FIG. 6. In FIG. 6 body weight (in kg, horizontal axis) is plotted against body height (in m, vertical axis) and the resulting BMI (weight in kg divided by height in meters) is shown as number in the table grid at the appropriate position.

In FIG. 7 the same table is presented including graphics of simulated approximated cross-sections as per FIG. 2 generated as described above for some selected extreme combinations of body height and body weight. In particular, there is shown a set of simulated thoracic cross-sections for small body height (1.5 m) and varying body weight (35 kg, 45 kg, 55 kg, 65 kg, 75 kg and 85 kg) and a set for large body height (2.1 m) and varying body weight (65 kg, 85 kg, 105 kg, 125 kg and 145 kg), furthermore one graphic for the body height of 1.9 m and the body weight of 145 kg.

The simulated thoracic cross-sections result from CT investigations of a plurality of persons, as described above, and were generated based on the regression calculations described in the text (see above paragraphs "Statistical analysis" and "Building an approximate slice") using subject body height, body weight (the gender is male, and age fixed at 45 years).

It was surprisingly found that the simulated thoracic cross-sections (and hence also the 3D anatomical models that may be built from them) of extreme small body height usually can be extrapolated to a simulated thoracic cross-sections of extreme large body height, whereby the corresponding simulated thoracic cross-sections have the same proportions as their small counterpart. Thus in general terms, it can be said that extreme cross sections of very small and very tall types match in their shapes and contour arrangement. In FIG. 7 the extreme simulated thoracic cross-section counterparts of small and large body height are graphically connected via the dotted lines of the double arrows.

Furthermore, surprisingly simulated thoracic cross-sections of intermediate body height, match in their size relationship with the extremes under the same dotted line, see FIG. 7. The dotted lines connect cross-sections that are essentially equivalent. The connected cross-sections differ merely in their absolute sizes, however not in the relative arrangement of the organ contours.

It can be noticed, that the dotted lines do not run along equal BMI numbers. In particular, the highlighted line numbers i, ii, and iii in FIG. 7 clearly show that they do not. Thus, this table illustrates that the BMI is a poor indicator of body and organ shape, because the dotted correlation lines between different body heights do not correlate with the BMI numbers indicated in the table.

Cross-sections lying on the same dotted line are practically equivalent, shape-wise and also in the context of EIT. Based on the in FIG. 7 presented line relations between corresponding extreme thoracic cross-sections, few base 3D models, for example 3 to 12 base thoracic 3D models, may be generated. FIG. 8 suggests, by way of example, 8 base thoracic 3D models, A to H, represented by their corresponding simulated cross-section slices. In FIG. 8 on the centre-line of the diagram (at 1.8 m body height), each body-mass index square is assigned to one particular organ shape called A through H. This makes 8 categories of organ shapes. Each category A through H is then assigned to the other squares above and below the centre-line, by following the dotted lines, as shown in FIG. 8. A library containing few base types of thoracic 3D models (e.g. A to H of FIG. 8) and an algorithm with an empirical rule for scaling said base models up and down suffices in order to match most of the population's individuals based on simple biometric data, including body height, body weight and optionally the gender and/or age.

Due to the discovered and herein presented empirical relation between thoracic cross-sections, body weight, body height and gender a library or lookup table 202 comprising few base type 3D models can be kept small and therefore needs little storage space. For example using 3 to 15, 5 to 12, or about 8, basic thoracic 3D models from which one is selected based on a patient's biometric data. Above refers to adults. For children, the library had to be extended for different age groups.

Scheme

Figure 10:
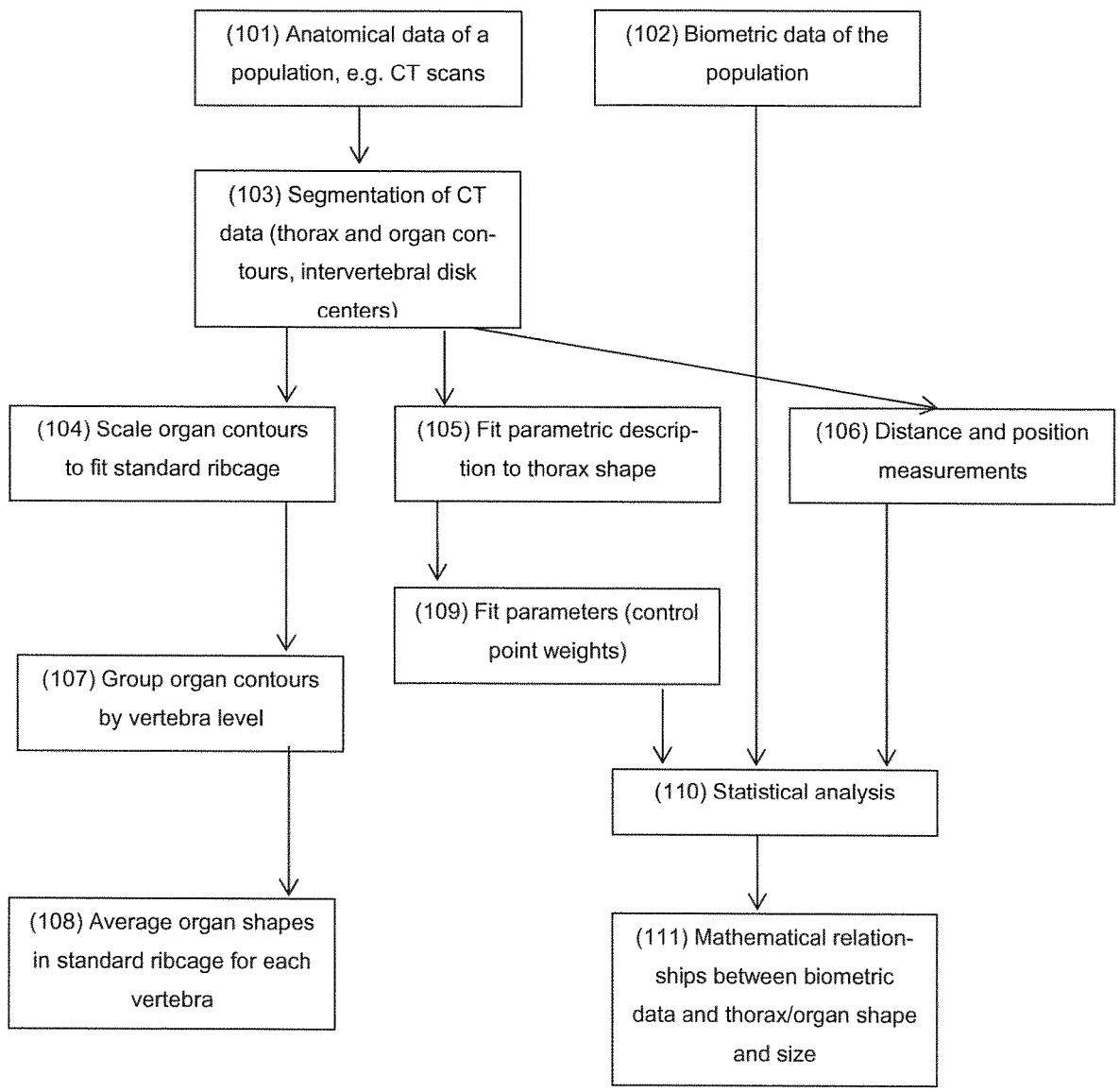
FIG. 10 shows a scheme of a process of creating average organ shapes in a standard ribcage for each vertebra and mathematical relationships between biometric data and body and organ shapes and sizes.

In FIG. 10 is summarized the process of creating standardized average organ shapes for each vertebra of a thorax and mathematical relationships between biometric data and body and organ shapes and sizes based on a study of the thorax shape and size in a population.

CT data of a population 101 are segmented 102: in the transverse plane organ contours are outlined (as in FIG. 2); in the sagittal plane intervertebral disk centers are marked 103. From those, various distance and position measurements 106 are extracted (those shown in FIG. 2 plus disk-to-disk distances). Separately, organ contours are scaled to fit a standard ribcage size 104, grouped by the vertebra the originating transverse slice intersects 107, and average organ shapes are calculated 108, one per vertebra. (Paragraph: "Data processing"). "Shape" refers to a cross-section plane. "Standard" means that each set of organ contours originating from segmentation of the CT data is scaled to fit a rectangle (bounding box) of the same specific size X times Y. "Average" refers to shape averaging, once all shapes are scaled to the same rectangle.

A parametric (spline) description of a thorax shape is fitted to the segmented thorax contour in each transverse slice 105 in each patient, resulting in a set of control point weights 109 (Paragraph: "Parametric description of thorax shape").

The extracted distance measurements 106 and shape descriptors 109 are related to the biometric data 102 by statistical modeling 110 (for example using ordinary least square regression), resulting in a set of mathematical formulae 111, one per measurement/descriptor, allowing the prediction of the measurement/descriptor based on biometric data.

Figure 11:
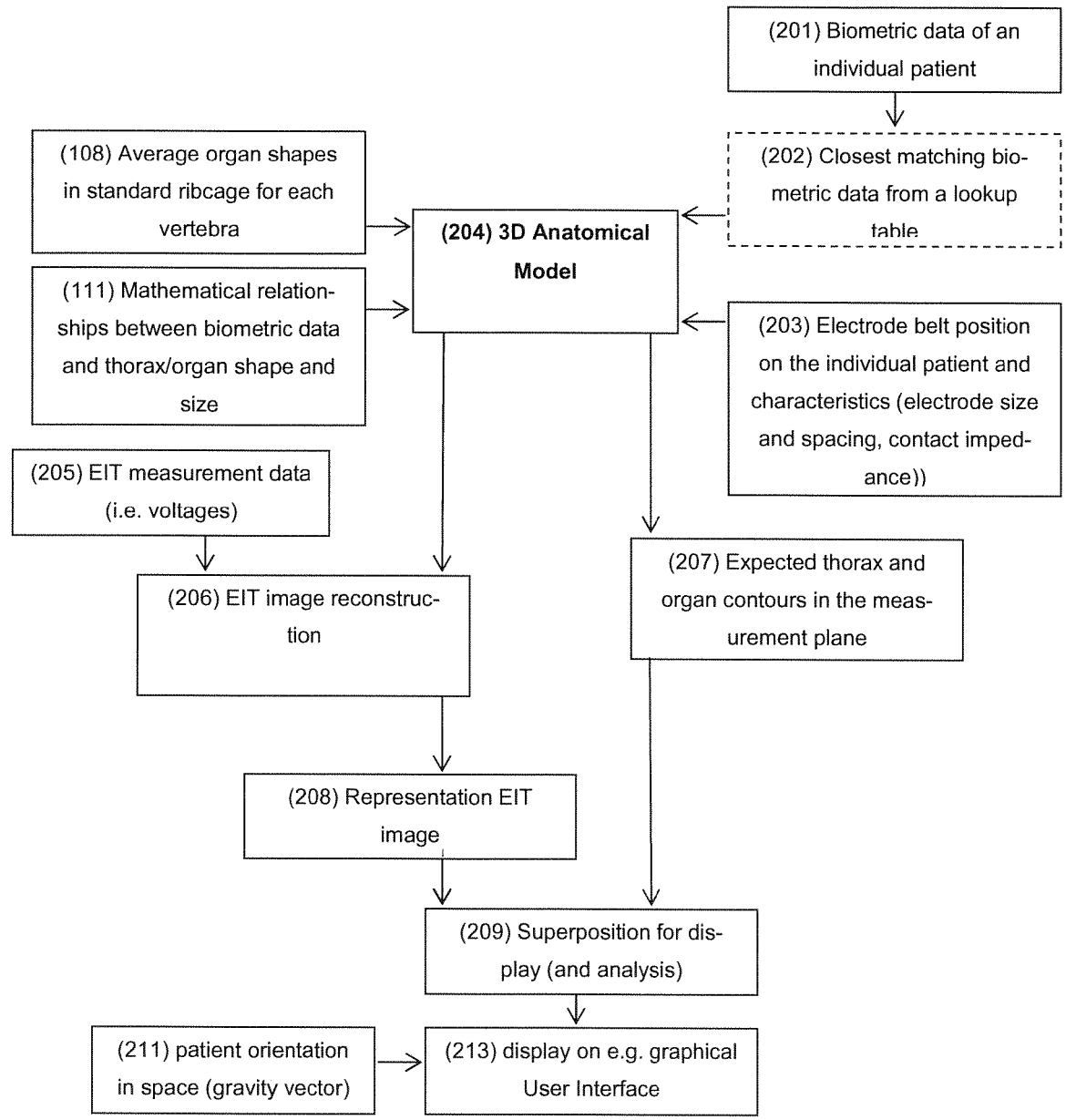
FIG. 11 shows a scheme of operation of present inventive system.

In FIG. 11 is summarized the operation of the system of present invention.

The stored average organ shapes 108 and mathematical relationships between biometric data 111 are used together with biometric data of an individual patient 201 and information about the electrode belt placement and characteristics 203 to generate an individualized 3D anatomical model of the thorax (FIG. 5) (Paragraph: "3D Models"). Optionally, the patient's true biometric data may be approximated to the closest available value using a lookup table (as in FIGS. 7 and 8). In that case, the models (now limited in number by the lookup table) may be stored rather than built on the device.

For example if a lookup table is used, then the total number of permissible height/weight/gender combinations is predetermined. That means that rather than build a model specifically for e.g. a 178.3 cm, 86.4 kg male, a model for 175 cm, 85 kg male which is stored on the device is used.

The 3D model 204 is used to reconstruct 206 measured EIT data 205 into an EIT image 208. In special cases, the reconstruction process involves a multiplication by a so called Reconstruction Matrix (RM) which is calculated based on the 3D model. If this is the case, and if a lookup table is used to limit the number of the 3D models, then the number of RMs is also limited and so may be stored on the device. This obviates the need to store the 3D models on the device.

Based on the 3D model 204 and the positioning of the electrode belt 203, a cross-section of the 3D model along the plane defined by the electrode belt is calculated, which defines the expected organ contours in the EIT image 207. Those contours are overlaid on the image 209 and may also be used to group pixels of the EIT image according to the organ they fall into for analysis.

In case where the 3D model 204 is neither stored nor generated by the device on the fly (i.e. it is generated earlier and relevant information is embedded into the limited number of RMs), the expected contours 207 must be stored on the system.

The superposition 209 may be displayed on a graphical user interface 213. If orientation and/or position of the patient 211 during EIT measurement is known, e.g. due to determination of the orientation and position of the patient (or the electrode belt) with regard to the gravity vector, the display 213 may indicate such orientation and position.

Example

EIT data measurement and evaluation on a particular patient comprising the steps of:

For a particular patient one of the patient-category-specific models (which is e.g. stored in storage such as reference numeral 25 of FIG. 1) is selected based on the patient's body height, body weight and optionally the gender (which were e.g. entered via an input interface such as reference numeral 29 of FIG. 1).

EIT and gravity vector data of the patient are measured (e.g., simultaneously).

The selected 3D anatomical model is used in reconstructing the EIT image from the measured voltages, here specifically for calculation of a patient-category specific reconstruction matrix.

The 2D organ contour is associated with the selected patient-category-specific 3D anatomical model for display on a graphical user interface (GUI). The display on the GUI serves as a reference platform for the reconstructed EIT image, in that the selected patient-category-specific contour and the patient's reconstructed EIT image may be presented in a superposed combination, see FIG. 9.

Figure 9:
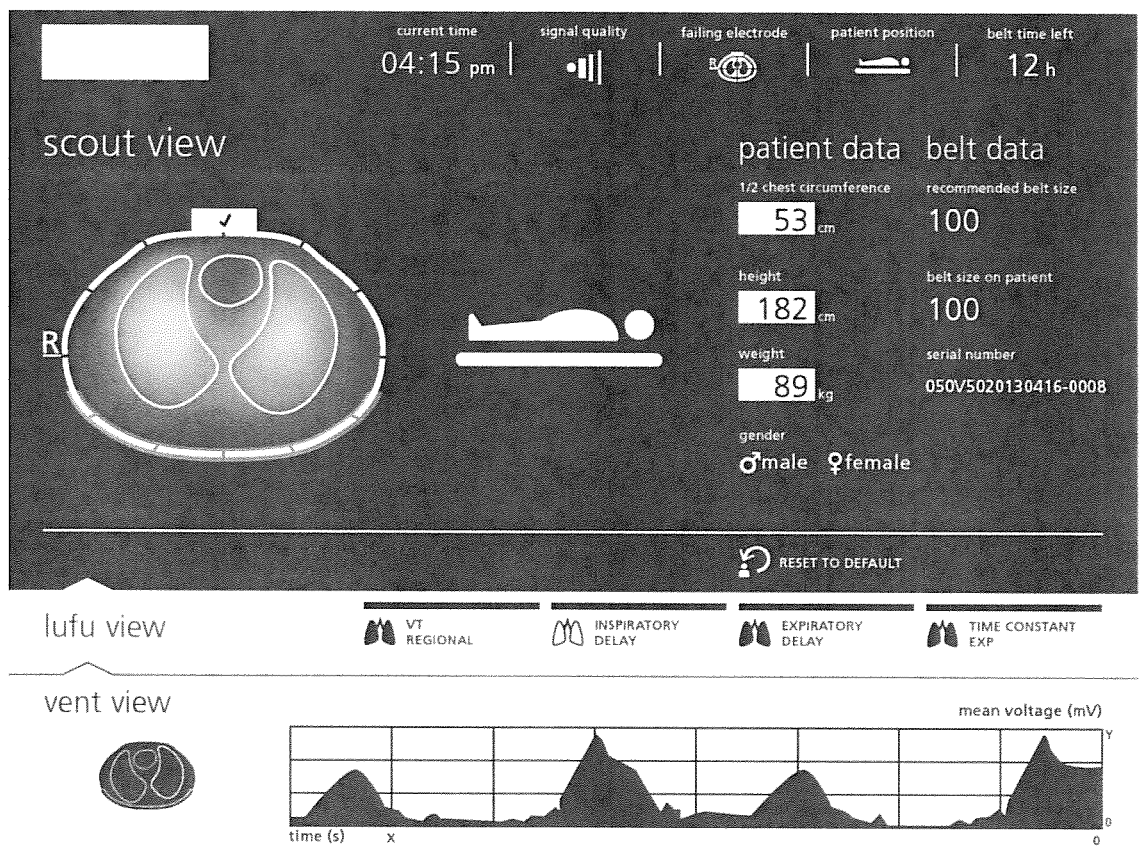
FIG. 9 shows a graphical user interface presenting a patient's EIT image within a selected patient-category-specific contour, a position indicator, patient specific biometric data, and electrode belt data.

Optionally, in order to ease intuitive interpretation of the EIT data, the orientation of the patient in space relative to the gravity vector is indicated on the GUI by rotating the selected patient-category-specific contour and the EIT image and by additional patient position indicators, see FIG. 9.

As a result, the EIT images on display are mathematically correctly reconstructed and thus specific for an individual patient, they are displayed in correct proportions and may be in a correct relation to the gravity vector.

Above embodiments and examples are intended to illustrate the art of the present invention and are not intended to limit the scope of the claims below.

While the invention has been described above with reference to specific embodiments and examples thereof, it is apparent that changes, modifications, and variations can be made without departing from their inventive concept disclosed herein. Accordingly, it is intended to embrace all such changes, modifications and variations that fall within the spirit and broad scope of the appended claims.

The invention claimed is:

1. An electrical impedance tomography (EIT) system for determining electric properties of an internal body part of a patient comprising:

an electrode array arranged on a sensor belt and adapted to be in electrical contact with an external surface of a body of a patient;

a device for applying an electrical current or voltage between two or more electrodes of the electrode array and for measuring at least one of generated electrical voltages or currents between other pair combinations of the electrode array;

a computing unit comprising a data processor and a storage unit, the storage unit comprising at least one reconstruction algorithm for use by the data processor for reconstructing measured electrical voltages of the internal body part into at least one of electrical properties or changes of electrical properties of the internal body part, the data processor adapted to output a representation of the reconstructed electrical properties, and to generate or process a plurality of anatomical models descriptive of the body part comprising a transversal slice of a human thorax including a shape of a thorax contour and organ shapes, the data processor adapted to choose an anatomic model for reconstruction of an EIT image in an EIT measurement plane determined by positions of electrodes of the electrode array on the external surface of the body; and an input interface for inputting biometric data of the patient for use by the data processor, the data processor adapted to select one anatomical model of the plurality of anatomical models on account of the biometric data of the patient and to use the selected one anatomical model of the plurality of anatomical models for reconstructing the measured electrical voltages of the body part into electrical properties or changes of electrical properties;

wherein the one of the plurality of anatomical models is a statistics based anatomical model and is based on a statistical description of a population; and wherein the data processor is adapted to output a cross-sectional image of the selected one anatomical model of the plurality of anatomical models, the cross-sectional image consisting of contour lines of the external surface of the body and internal organs, in the EIT measurement plane, and the processor is adapted to generate for display a superposed combination of a representation of reconstructed electrical properties and the cross-section image of the anatomical model, wherein contours delineating the external surface of the body and the internal organs overlay the representation.

2. The system of claim 1, wherein the biometric data comprise at least body weight and body height.

3. The system of claim 1, wherein a position of individual electrodes of the electrode array are accounted for by at least one of the plurality of anatomical models and the input interface allows input of or is adapted to read electrode array characteristics and position on the patient.

4. The system of claim 1, wherein the electrode array is selectable from several different sizes in order to account for anatomical constitution of the patient.

5. The system of claim 1, wherein the belt is configured to be positioned around a thorax of the patient.

6. The system of claim 5, wherein the belt carries an identifier that is readable by the data processor.

7. The system of claim 6, wherein the identifier carries information about a number of electrodes of the electrode array.

8. The system of claim 1, wherein distances between neighboring electrodes of the electrode array are predetermined.

9. The system of claim 1, wherein the at least one reconstruction algorithm is adapted to take account of a number of electrodes of the electrode array.

10. The system of claim 1, further comprising a sensor for determining an orientation of an EIT measurement plane with respect to a gravity vector for determining a spatial orientation of a body section of the patient.

11. The system of claim 10, wherein the electrode array carries the sensor for determining the orientation.

12. The system of claim 1, wherein the data processor is adapted to use position data as input for a display algorithm in order to display patient position.

13. The system of claim 10, wherein the processor is adapted to display the representation in alignment with at least one of the gravity vector or with respect to an indicator of the gravity vector.

14. The system of claim 1, further comprising contours used to group a plurality of pixels of the representation based on which contour the group of the plurality of pixels fall in.

15. The system of claim 1, wherein the representation is an image or matrix of a distribution of the electrical properties.

16. The system of claim 1, wherein the storage unit comprises information for providing the plurality of anatomical models for use by the data processor for reconstruction, wherein the information is provided in a library or within an algorithm.

17. The system of claim 1, wherein the processor is adapted to generate or recall from storage the plurality of anatomical models on account of biometric data of the patient and of biometric data of a population.

18. The system of claim 1, wherein the processor is adapted to generate the plurality of anatomical models on account of a statistical description of the population and biometric data, information on the patient, and information on electrodes of the electrode array.

19. The system of claim 1, wherein the processor is adapted to generate the plurality of anatomical models on account of shapes of a body and an organ of a plurality of standardized ribcages, and mathematical relationships describing statistical relations between biometric data and shapes of the body and the organ of a population.

20. The system of claim 19, wherein the mathematical relationships account for biometric data of a population and anatomical data of a population.

21. The system of claim 20, wherein the organ shapes of a standardized ribcages originates from anatomical data.

22. The system of claim 1, wherein the one of the plurality of anatomical models is a three dimensional anatomical model.

23. The system of claim 1, wherein the processor is adapted to use a lookup table to select an anatomical model, the lookup table comprising exemplary cross-sectional contour models for some combinations of body height and body weight, and a rule for indication of tracks between various coordinates of body height and body weight connecting those coordinates relating to cross sectional contours of empirically assumed constant dimensional proportions.

24. The system of claim 23, wherein the processor selects one of the plurality of anatomical models on account of the biometric data of the patient.

25. The system of claim 24, wherein the processor is adapted to select from at least two lookup tables comprising a gender specific lookup table, an age specific lookup table and a race specific lookup table.

26. The system of claim 25, wherein exemplary cross-sectional contour models range from a slim type to an obese type.

27. The system of claim 1, further comprising a system for providing anatomic data comprising at least one of an x-ray computed tomography system, a magnetic resonance imaging system, or an imaging system capable of providing anatomically accurate cross-sections of a human body.

* * * * *